United States Patent
Nitsch et al.

(10) Patent No.: US 6,329,155 B1
(45) Date of Patent: Dec. 11, 2001

(54) METHODS OF IDENTIFYING AGENTS WHICH REGULATE RELEASE OF AMYLOID PRECURSOR PROTEIN

(75) Inventors: Roger M. Nitsch, Boston; Barbara E. Slack, Cambridge; Richard J. Wurtman, Boston; John H. Growdon, Chestnut Hill, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/228,078

(22) Filed: Apr. 15, 1994

Related U.S. Application Data (63) Continuation-in-part of application No. 07/959,253, filed on Oct. 9, 1992, now abandoned.

(51) Int. Cl.[7] .................. G01N 33/567; G01N 33/53; C12P 21/06

(52) U.S. Cl. .................. 435/7.21; 435/7.21; 435/69.1; 436/815

(58) Field of Search .................. 435/7.21, 69.1; 530/388.85, 389.1; 436/815

(56) References Cited

U.S. PATENT DOCUMENTS

| | | | |
|---|---|---|---|
| 5,242,932 | * | 9/1993 | Gandy et al. .................. 514/313 |
| 5,348,963 | * | 9/1994 | Gandy et al. .................. 514/313 |
| 5,385,915 | * | 1/1995 | Buxbaum et al. .................. 514/313 |

FOREIGN PATENT DOCUMENTS 0 457 295 A2  11/1991  (EP) .

OTHER PUBLICATIONS

Buxbaum et al, "Processing of Alzheimer B/A4 amyloid precursor . . . " *PNAS* 87:6003–6006 (Aug. 1990).*

Weidemann et al, "Identification, Biogenesis, and Localization of Precursors of Alzheimer's Disease A4 Amyloid Protein", *Cell* 57:115–126 (Apr. 1989).*

Palmert et al, "The B–amyloid protein precursor of Alzheimer's disease . . . " *PNAS* 86:6338–6342. (Aug. 1989).*

Sandmann et al, "Coupling of Transfected Muscarinic Acetycholine Receptor Subtypes . . . ", *J. Biol. Chem.* 266(10):6031–6034 (Apr. 1991).*

Peralta et al, "Differential regulation of PI hydrolysis and adenyl cyclase by muscarinic receptor subtypes", *Nature* 334:434–437 (Aug. 1988).*

Selkoe et al, "B–Amyloid precursor protein of Alzheimer disease . . . " *PNAS* 85:7341–7345.*

Tsunao Saitoh, et al., "Aberrant Protein Kinase C Cascades in Alzheimer's Disease", *Adv. Exp. Med. Biol.* 265:301–310 (1990).

Gregg L. Caporaso, et al., "Protein phosphorylation regulates secretion of Alzheimer β/A4 amyloid precursor protein", *Proc. Natl. Acad. Sci. USA* 89:3055–3059 (1992).

Abha Chauhan, et al., "Action of Amyloid Beta–Protein on Protein Kinase C Activity", *Life Sciences* 49:1555–1562 (1991).

(List continued on next page.)

Primary Examiner—Gray L. Kunz
(74) Attorney, Agent, or Firm—Pepper Hamilton LLP; Gilberto M. Villacorta; Corinne M. Pouliquen (57) ABSTRACT

Amyloid precursor protein (APP) processing which is activated by cell-surface neurotransmitter receptors, is described. An assay for testing an agent for the capacity to regulate, and particularly to stimulate, secretion of amyloid precursor protein (APP), a description of the characteristics of agents identified by the assay, and a method of altering APP processing in an individual are also disclosed. The assay, agents, and method of altering APP processing are particularly useful for the treatment and prevention of diseases involving APP processing, such as Alzheimer's disease.

8 Claims, 5 Drawing Sheets

OTHER PUBLICATIONS

Samuel Gandy, et al., "Phosphorylation of Alzheimer Disease amyloid precursor peptide by protein kinase C and $Ca^{2+}$/calmodulin–dependent protein kinase II", *Proc. Natl. Acad. Sci. USA* 85:6218–6221 (1988).

Jennifer S. Kiefer–Day, Esam E. El–Fakahany, "Muscarinic Receptor Function and Acetylcholinesterase Activity After Chronic Administration of Tacrine to Mice at Therapeutic Drug Concentrations", *Pharmacology* 44:71–80 (1992).

David H. Small, et al., "A Protease Activity Associated with Acetylcholinesterase Releases the Membrane–Bound Form of the Amyloid Protein Precursor of Alzheimer's Disease", *Biochemistry* 30:10795–10799 (1991).

T. Suzuki, et al., "Phosphorylation of Alzheimer Amyloid Precursor Protein by Protein Kinase C", *Neuroscience* 48(4):755–761 (1992).

Shun Shimohama, et al., "Acetylcholine receptors in Alzheimer–type Dementia", Recent research on neurotransmitter receptors. Proceedings of the 2nd Workshop on Neurotransmitters & Disease, Tokyo, Jun. 15, 1985. Yoshida, H. (ed)., *Experpta Medica*, 1986. *Excerpta Medica*, Int'l Congress Series No. 710) pp. 2–12.

Krogsgaard–Larsen, P., "Alzheimer's Disease: Acetylcholine and Glutamic Acid Receptors as Therapeutic Targets", *Act. Chim. Ther.* 17:161–73 (1990).

Nitsch, R.M. et al., "Release of Alzheimer Amyloid Precursor Derivatives Stimulated by Activation of Muscarinic Acetylcholine Receptors," *Science* 258;304–307 (1992).

Peralta, E.G., et al., "Differential regulation of PI hydrolysis and adenylyl cyclase by muscarinic receptor subtypes," *Nature* 334:434–437 (1988).

Golde, T.E. et al., Processing of the Amyloid Protein Precursor to Potentially Amyloidogenic Derivatives, *Science* 255:728–730 (1992).

Estus, S., et al., "Potentially Amyloidogenic, Carboxyl–Terminal Derivatives of the Amyloid Protein Precursor," *Science* 255:726–728 (1992).

* cited by examiner

METHODS OF IDENTIFYING AGENTS WHICH REGULATE RELEASE OF AMYLOID PRECURSOR PROTEIN

RELATED APPLICATIONS

This application is a Continuation-in-Part (CIP) of U.S. Ser. No. 07/959,253, filed Oct. 9, 1992, now abandoned, teachings of which are incorporated herein by reference.

FUNDING

This work was supported by the NIMH, NIA, and the Center for Brain Sciences and Metabolism Charitable trust.

DESCRIPTION

Background

Alzheimer's disease (AD) is a chronic progressive neurodegenerative disease. Clinically, it is characterized by progressive deficits in memory and other cognitive functions that occur in the face of an otherwise normal neurological examination. Postmortem examination reveals a variety of typical AD brain lesions, including deposition of amyloid plaques, formation of neurofibrillary tangles, and neuronal degeneration.

The amyloid deposits characteristic of AD pathology consist of aggregates of a 39–42 amino acid peptide termed β/A4 (G. G. Glenner and C. W. Wong, *Biochem. Biophys. Res. Comm.*, 120:885 (1984); C. L. Masters et al., *Proc. Natl. Acad. Sci. USA*, 82:4245 (1985); D. J. Selkoe et al., *J. Neurochem.*, 46:1820 (1986)), which is an abnormal cleavage product of a larger amyloid precursor protein (APP) (J. Kang et al., *Nature*, 325:733 (1987)). APP is an integral membrane glycoprotein, existing as several distinct forms derived from alternative mRNA splicing (R. E. Tanzi et al., ibid, 331:528–530 (1988); P. Ponte et al. ibid, 331:525 (1988); N. Kitaguchi et a., ibid., 331:530 (1988)). Water-soluble APP fragments lacking the COOH terminus have been detected in conditioned cell culture media and in human cerebrospinal fluid (A. Weidemann et al., *Cell*, 57:115, (1989), M. R. Palmert et al., *Proc. Natl. Acad. Sci. USA*, 86:6338 (1989)), indicating that APP is a secretory protein. Normal secretion of water-soluble $NH_2$-terminal APP fragments involves cleavage of full-length APP at an extracellular site located close to the transmembrane domain, and within the β/A4 domain (T. Oltersdorf et al., *Nature*, 341:144 (1989); F. S. Esch et al., *Science*, 248:1122 (1990); S. S. Sisodia et al., ibid., 248:492 (1990); J. P. Anderson et al., *Neurosci. Lett.*, 128:126 (1991); R. Wang et al., *J. Biol. Chem.*, 262:16960 (1991)). This cleavage event presumably precludes the formation of amyloidogenic APP fragments. Alternatively to secretion, APP can be processed by an internal lysosomal pathway (C. Haass, A. Y. Hung, D. J. Selkoe, *J. Neurosci.*, 11:3783 (1991); C. Haass, E. H. Koo, A. Mellon, A. Y. Hung, D. J. Selkoe, *Nature*, 357:500 (1992)) that may generate amyloidogenic cleavage products (S. Estus et al., *Science*, 255:726 (1992); T. E. Golde, S. Estus, L. H. Younkin, D. J. Selkoe, S. G. Younkin, ibid., 255:728 (1992)). It is therefore likely that aberrations of APP processing pathways contribute to amyloid formation. The mechanisms regulating cellular APP processing, however, are unknown.

SUMMARY OF THE INVENTION

This invention is based on the results of an assessment of control of APP processing in cells. As described herein, it has been discovered that cell-surface neurotransmitter receptors regulate APP processing. In particular, it has been shown that cellular APP release is controlled by cell-surface neurotransmitter receptor activity (i.e., APP release is "triggered" or signaled by activation of cell-surface neurotransmitter receptors), and that the regulatory effect on the release of APP derivatives is receptor-subtype specific (i.e., is controlled or signaled by activation of cell-surface neurotransmitter receptors which are linked to phospholipase and a protein kinase, such as protein kinase C (PKC)). This work has resulted in the description of a novel cell-surface neurotransmitter receptor-mediated mechanism for the stimulation of release of soluble $NH_2$-terminal APP derivatives.

Human cells expressing the m1 or m3 subtypes of the human brain muscarinic acetylcholine receptor (mAChR) have been shown to be activated by cholinergic agonists, and, as a result, to release a water-soluble NH2-terminal cleavage product of APP which lacks the COOH terminal portion. This stimulation and associated APP processing is blocked by muscarinic antagonists. In contrast, basal release of APP fragments from wild-type cells and from cells expressing subtypes m2 or m4 mAChR receptors is not stimulated. These results indicate that neurotransmitter-control of the release of APP derivatives is receptor subtype-specific, presumably due to the differential coupling of the receptor subtypes to distinct second messenger systems (E. G. Peralta, A. Ashkenazi, J. W. inslow, J. Ramachandran, D. J. Capon, *Nature*, 334:434 (1988); J. Sandmann, E. G. Peralta, R. J. Wurtman, *J. Biol. Chem.* 266, 6031 (1991)): activation of the phospholipase C-linked mAChR subtypes m1 and m3 stimulated APP release, whereas the adenylyl cyclase-linked subtypes m2 and m4 did not mediate this response.

In addition to mAChR subtypes m1 and m3, bradykinin receptors and serotonin receptor subtypes $5HT_2$ and $5HT_{1C}$ demonstrate specific control of the release of APP derivatives. Therefore, these and other receptors linked to phospholipase and a protein kinase, such as protein kinase C, can be used to identify substances which cause release of non-amyloidogenic APP fragments and therefore may be useful for treatment of AD, as well as for preventing the formation of amyloidal plaques.

An assay based upon the above findings may be used to determine whether compounds which activate cell-surface receptors increase the proteolytic processing of APP along with increased release of NH2-terminal derivatives. In the assay of the present invention, the cells employed may be any mammalian or human cells which process and secrete APP normally, and which express an endogenous gene or an exogenous gene (i.e., a gene introduced into the cell, such as by transection) encoding a surface-expressed neurotransmitter receptor linked to phospholipase C and protein kinase C (PKC), such as AChR subtypes m1 and m3, bradykinin receptors, or serotonin receptors subtypes $5HT_2$ and $5HT_{1C}$. Such cells are referred to herein as test cells. A sample of the agent to be tested is contacted with cultured test cells; after incubation, the level of secretion of APP derivatives is measured. The amount of APP derivative released is compared to the level released by a control sample of the test cells under the same conditions but in the absence of the test agent. If the level of APP secretion in the presence of the test agent is less than the level of APP derivatives by the control, the test agent may have inhibited the receptor, and, thereby, decreased the secretion of APP derivatives. If the level of APP secretion in the presence of the test agent is the same as the level of APP derivatives by the control (i.e., in the absence of the agent), the test agent did not exhibit receptor-mediated regulatory activity on APP processing. If the level of secretion of APP derivatives in the presence of the agent is greater than the level of APP by the control, the test agent may have activated the receptors, and thereby increased secretion of APP derivatives.

To verify that the test agent stimulates the neurotransmitter receptors, the effect of an antagonist of the neurotransmitter receptors upon stimulation by the test agent can also be examined. If the receptor antagonist inhibits the stimulating effect of the test agent, then it is even clearer that the test agent is an activator of the receptors. Finally, the size and cleavage pattern of the secreted APP are determined by known methods (e.g., gel electrophoresis, western blot, or enzyme-linked immunosorbent assay (ELISA)), to determine whether the secreted fragment is a non-amyloidogenic fragment or an amyloidogenic fragment generated from pre-existing APP molecules in the cell. The agents identified through this assay may be useful in the treatment and prevention of AD: agents which alter APP processing in individuals by stimulating non-amyloidogenic APP processing, can thereby inhibit the amyloidogenic APP processing and formation of amyloidal plaques.

DETAILED DESCRIPTION OF THE INVENTION

The present invention relates to a discovery relating to regulation of processing of APP to produce water-soluble proteolytic cleavage products which lack the COOH terminal domain. As described herein, APP processing is stimulated by activation of specific subtypes of cell-surface neurotransmitter receptors. Activation of cell-surface neurotransmitter receptors which are linked to phospholipase C and to a protein kinase, such as protein kinase C (PKC), such as muscarinic receptors, bradykinin receptors and serotonin receptors, has been shown to regulate cellular APP processing and to increase the release of NH2-terminal APP derivatives. Activation of members of these cell-surface neurotransmitter receptor families, as described herein, results in enhanced release of APP $NH_2$-terminal fragments which are generated by cleavage of the APP molecule within the β/A4 segment, thus preventing the formation of amyloidogenic fragments. The term, "APP processing derivatives", is used herein to describe the APP fragments generated by APP processing in the cell, such as the NH2-terminal fragments.

The present invention encompasses a method of assaying an agent for the ability to regulate, and particularly to stimulate, the secretion of amyloid precursor protein (APP) in cell culture; the agents identified by the present assay method, and a method of altering APP fragment release in a cell. Identification of agents which stimulate APP secretion without creation of amyloidogenic fragments will be valuable in the search for substances which can be used to treat or to prevent AD. The agents which stimulate APP secretion in cultured cells can also be useful in vivo, as it is reasonable to infer that the agents will stimulate APP secretion in the targeted cells of a whole animal, including humans. Thus the invention also encompasses a method of altering APP processing in an individual and a method of treating or preventing amyloid deposition.

To test an agent for its ability to stimulate secretion of APP derivatives, any type of cells which cleave and secrete APP and express a cell surface neurotransmitter receptor which is linked to phospholipase C and a protein kinase, such as protein kinase C, may be used. The cells may express an endogenous gene encoding a cell surface neurotransmitter receptor or an exogenous gene encoding a cell surface neurotransmitter receptor introduced or transfected into the cells using known methods. In one embodiment, cultured human embryonic kidney (293) cells are used. The 293 cells normally express full-length human $APP_{751/770}$, secrete a large $NH_2$-terminal APP fragment cleaved within the APP within the β/A4 domain (herein referred to as a non-amyloidogenic APP derivative) and retain an 11.5 kD COOH-terminal APP fragment (T. Oltersdorf et al., *J. Biol. Chem.*, 265:4492 (199)), indicative of non-amyloidogenic APP processing by this cell line. Non-amyloidogenic APP processing, as used herein, indicates expression of APP, cleavage of APP within the β/A4 domain, thereby producing the $NH_2$-terminal APP derivative, and secretion of the derivative. The cells are transfected with the human genes for mAChR subtypes m1, or m3, and those stably producing mAChR are utilized in the assay.

In another embodiment, PC-12 cells which express the bradykinin receptor are used as the test cells. In yet another embodiment, cells which express serotonin receptor subtypes $5HT_2$ or $5HT_{1C}$ are used as test cells. Alternatively, other cell types which demonstrate non-amyloidogenic APP processing can be used, if they express endogenous neurotransmitter receptors. Cell types which endogenously produce receptors linked to activation of phospholipase C and a protein kinase, such as protein kinase C, are also appropriate.

The assay encompasses several sets of cell cultures: first, one culture for each receptor subtype present on the cell sample is exposed to the agent sought to be tested, by the addition of a sample of the agent to each culture; second, if the cell sample comprises cells transfected with genes to produce the receptors in question, then the agent is added to a control sample of non-transfected cells; and a final set of cultures for each receptor subtype is grown without the addition of any agent. After incubation for a brief time, preferably about 30 to 60 minutes under conditions appropriate for APP processing to occur, all samples are analyzed for the presence and level of secreted APP derivatives, using known methods, such as gel electrophoresis, western blot, and immunoreactivity using a monoclonal antibody directed against all or a portion of APP. Those agents which stimulate APP processing (i.e., stimulate production of APP fragments from APP molecules in the cells) are referred to herein as APP processing activators. Such agents can be known substances, such as those in chemical libraries or available from commercial sources, or substances present in microbial (e.g., bacterial, yeast) cultures. They can also be substances designed to activate a cell-surface neurotransmitter receptor of the subtypes described herein.

The level of increase of secretion caused by an APP processing activator is assessed, using known methods such as densitometric analysis of western blots or enzymelinked immunosorbent assay (ELISA). Preferably, the agent causes a several-fold increase in the level of secretion. For example, carbachol, an unspecific muscarinic agonist, caused a 3.9-fold increase in basal APP release in m1 transfected cells, and a 5.4-fold increase in m3 transfected cells. Assessment is also carried out to determine that the stimulation of the receptors generates secretion of $NH_2$-terminal, non-amyloidogenic APP fragments, rather than β/A4-containing amyloidogenic fragment. This can be performed using epitope-specific antibodies (e.g., polyclonal antiserum or a monoclonal antibody) against the β/A4-domain or the COOH terminus.

Once agents which enhance or inhibit APP secretion in cultured cells have been identified, these agents may be used in a method of altering APP fragment release in whole animals, including humans. Because it is now known that stimulation of cell-surface neurotransmitter receptors leads to enhanced non-amyloidogenic APP fragment release, and that inhibition of the receptors by antagonists suppresses this effect, it is reasonable to conclude that it is possible to alter APP fragment production in mammals, including humans, by administering an agent which has the same effect in vitro. In addition, an agent identified by the methods described can be used to inhibit or prevent the formation and deposition of amyloid in the brain, and thus be useful in both the treatment and the prevention of Alzheimer's disease, by increasing the formation of secreted, non-amyloidogenic, APP derivatives and simultaneously decreasing formation of amyloidogenic derivatives.

The agent identified by the current methods can be administered orally, by subcutaneous or other injection, intravenously, parenterally, transdermally, rectally or via an implanted reservoir. The form in which the agent will be administered (e.g., powder, tablet, capsule, solution, emulsion) will depend on the route by which it is administered. The quantity of the agent to be administered will be determined on an individual basis, and will be based at least in part on consideration of the individual's size and the result sought. The agent can be administered with other components; the components included in a particular composition are determined primarily by the manner in which the composition is to be administered. For example, a composition to be administered orally in tablet form can include, in addition to the agent, a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the agent and, optionally, an emulsifying agent, a flavoring agent, and/or a coloring agent.

The invention is illustrated by the following examples, which are not to be construed as limiting in any way.

EXAMPLE 1

Regulation of APP Processing by Muscarinic Receptor Subtypes

A. Transfection and Growth of 293 Cell Lines

Cultured human embryonic kidney (293) cell lines were utilized. The 293 cells were transfected with the genes for human brain muscarinic acetylcholine receptors (mAChR) subtypes m1, m2, m3, or m4, as well as for neomycin resistance as described (E. G. Peralta, A. Ashkenazi, J. W. Winslow, J. Ramachandran, D. J. Capon, *Nature*, 334:434 (1988)). The nomenclature for the mAChR subtypes used in this report follows the recommendation of the Muscarinic Receptor Nomenclature Committee, *Trends Pharmacol. Sci.* (suppl.),p. VII (1989)). Cells were grown in DMEM/F-12 medium containing 10% fetal bovine serum (Gibco) in the presence of the neomycin analog G-418 (0.5 mg/ml) (Geneticin, Gibco). As a control, nontransfected human 293 cells were obtained from the American Tissue Type Collection (no. CRL 1573) and maintained in the absence of G-418. The cell lines expressed a specific number of receptors per cell: m1, 350,000; m2, 120,000; m3, 200,000; m4, 50,000; wild-type, <300.

It is important to note that the transfected cell lines used in these experiments express larger than normal numbers of muscarinic receptors. However, other studies demonstrated that stimulation of endogenous neurotransmitter receptors in non-transfected, differentiated PC-12 cells also increased the release of APP fragments, indicating that physiologic receptor levels are sufficient to mediate this response (See Example 2).

B. Stimulation and Inhibition of the Muscarinic Acetylcholine Receptors

Confluent cell cultures on poly-D-lysine-coated ($M_r$>300,000; 0.1 mg/dish) culture dishes were washed with serum-free N-2 medium (Gibco) and incubated for 30 or 60 minutes in serum-free N-2 with or without 1 mM carbachol (Sigma), 10 μM atropine (Sigma), or 1 μM staurosporine (Sigma), or 10 μm A237 (Sigma), in the absence of G-418. Conditioned media were centrifuged at 10,000×g (4° C., 5 minutes), desalted on SEPHADEX G-25 columns (Pharmacia) with water as eluent, lyophilized, and reconstituted typically in 150 μl SDS loading buffer. Total cell protein per dish was measured with the bicinchoninic acid assay (Pierce). Cell proteins were not altered by any of the above treatments.

Figure 2A:
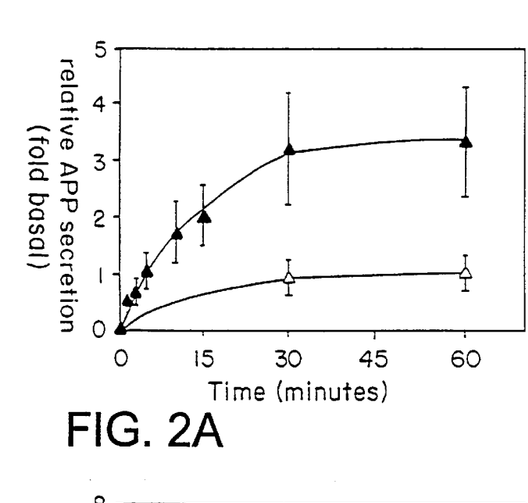
FIG. 2A, FIG. 2B, FIG. 2C, and FIG. 2D are graphic representations of time-(2A,2B) and concentration-dependent (2C,2D) APP release by human 293 cell lines transfected with the genes for the human m1 (triangles) and m3 (circles) mAChR subtypes in response to receptor activation by carbachol (CCh). (2A,2B): filled symbols, CCh; open symbols, vehicle controls. (2C,2D): filled symbols, CCh; open symbols, CCh in the presence of atropine (10 $\mu$M). For the time-courses, the carbachol concentration was 1 mM; for the dose-response curves, a 30 min incubation period was used. Data are means±S.E.M. of representative experiments with triplicate cell culture dishes (2A,2B,2C), and the means of two experiments with triplicate culture dishes (2D).
Figure 2B:
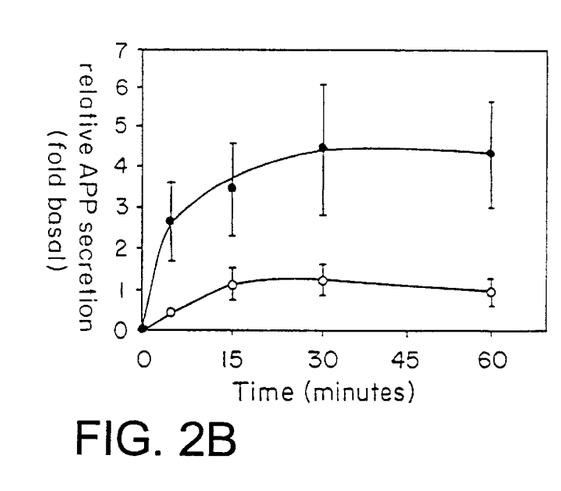

The results indicated that activation by the cholinergic agonist carbachol in cells expressing the genes for the m1 and m3 mAChR subtypes potently stimulated the release of water-soluble APP fragments into the cell culture media. The effect of both m1 and m3 mAChR stimulation on APP release was rapid: half-maximal stimulation was reached within 5 to 10 minutes, and the maximum was attained within 15 to 40 minutes (FIGS. 2A and 2B). These time-course experiments strongly suggest that preexisting cellular APP was processed in response to receptor activation. Using pulse-chase methods, Weidemann et al. (A. Weidemann et al., *Cell,* 57:115 (1989), M. R. Palmert et al., *Proc. Natl.*

*Acad. Sci. USA*, 86:6338 (1989)) showed that secreted forms of APP do not appear in the medium until 45 minutes after labelling.

Figure 2C:
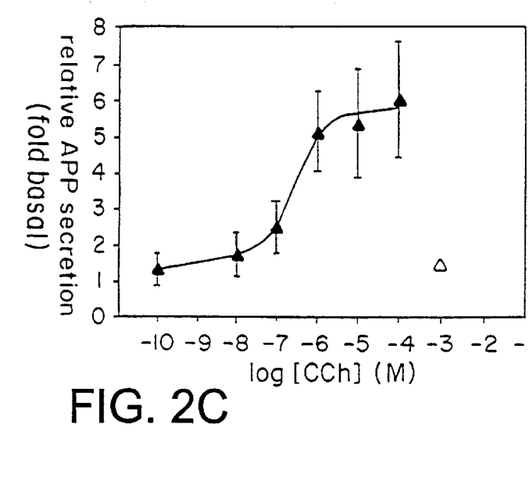
Figure 2D:
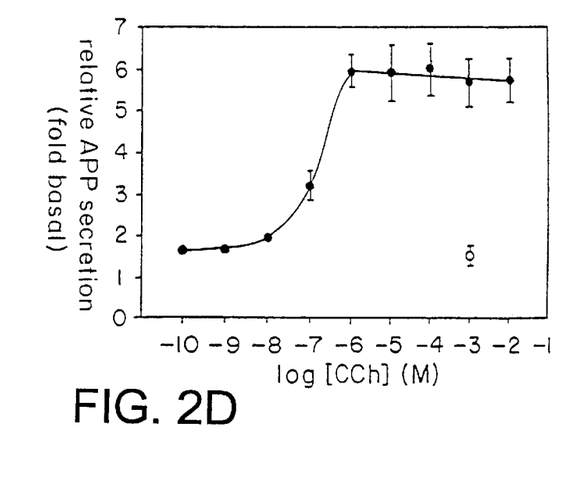

Stimulation of APP release by carbachol also showed a clear dose-response relationship (FIG. 2C and FIG. 2D), and the $EC_{50}$ values of 0.4 μM for the m1 and 0.15 μM for the m3 transfected cells were virtually identical to those obtained for receptor-coupled phosphatidylinositol turnover in the same cells.

Figure 1A:
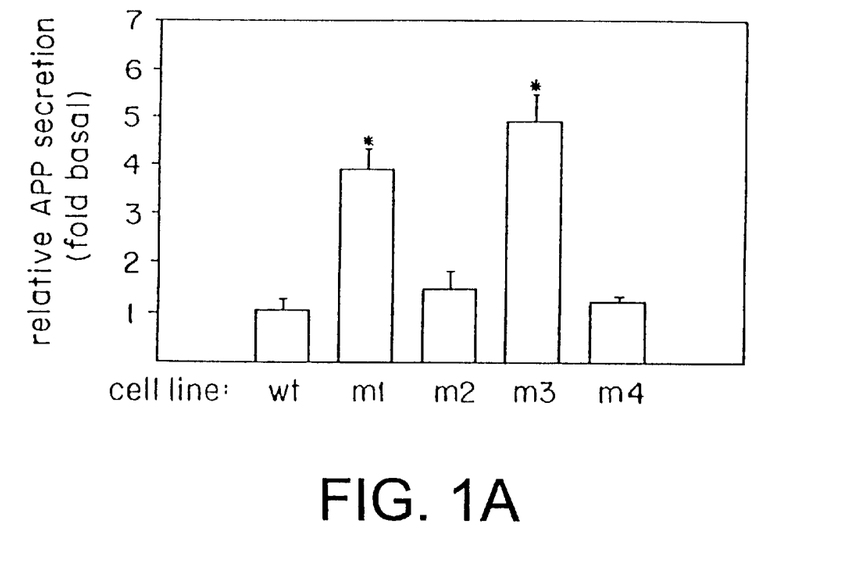
FIG. 1A and FIG. 1B are graphic representations of densitometric analysis of secreted APP fragments after stimulation with carbachol (*P<0.01 versus basal APP release, Mann-Whitney rank sum tests) and under various other conditions (i.e., *P<0.01 versus CCh-induced APP release, analysis of variance and post-hoc Scheffe tests). Bars indicate means±S.E.M. of 5–7 experiments. Key: CCh, carbachol; Atr, atropine; Stau, staurosporine; A23, calcium ionphore A23187; wt, wild-type.
Figure 1B:
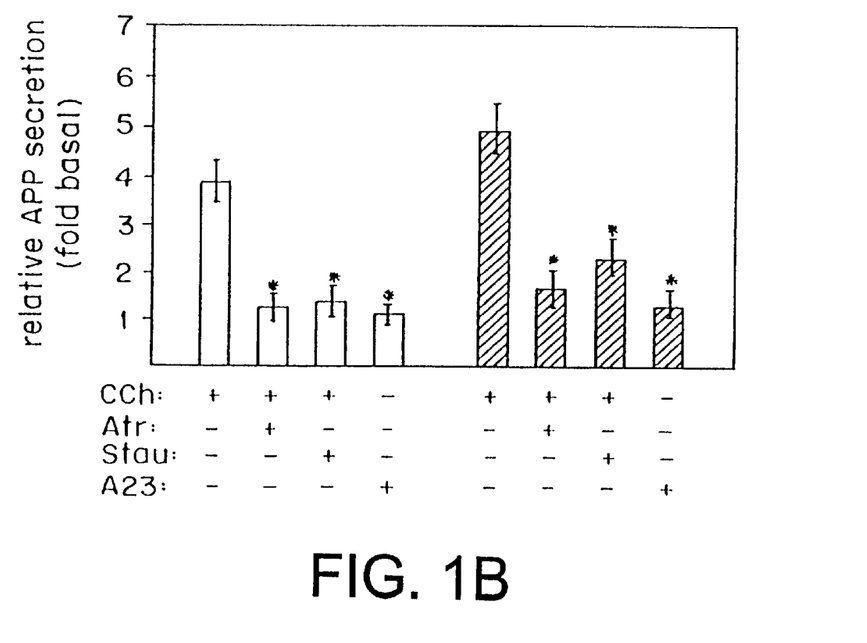

Receptor-activated APP release by both m1 and m3 transfected cell lines was blocked by the muscarinic antagonist atropine, indicating a specific agonist-receptor interaction (FIG. 1B). The effect of carbachol was also inhibited by staurosporine, suggesting phosphorylation, presumably by protein kinase C (PKC) activation (FIG. 1B). Stimulation of m1 and m3 receptors activates PKC via diacylglycerol formation (Nishizuka, *Science* 233, 305 (1986)), which, along with inositol phosphate, is a product of phosphatidylinositol hydrolysis (E. G. Peralta, A. Ashkenazi, J. W. Winslow, J. Ramachandran, D. J. Capon, *Nature*, 334:434 (1988); J. Sandmann, E. G. Peralta, R. J. Wurtman, *J. Biol. Chem.* 266, 6031 (1991)). Receptor-coupled APP release may thus be mediated by diacylglycerol-induced PKC activation, or by an interaction of diacylglycerol and calcium released from internal pools by inositol triphosphate (M. J. Berridge, R. F. Irvine, *Nature* 341, 197 (1989)). PKC activation by phorbol esters has been previously shown to increase both the release of $NH_2$-terminal APP fragments as well as the abundance of cell-associated COOH-terminal APP cleavage products in PC-12 cells, and to phosphorylate APP at $Ser^{655}$ in semi-intact PC-12 cells (G. L. Caparaso, S. E. Gandy, J. D. Buxbaum, T. V. Ramabhadran, P. Greengard, *Proc. Natl. Acad. Sci. U.S.A.* 89, 3055 (1992); Buxbaum et al., *Proc. Natl. Acad. Sci. U.S.A.* 87, 6003 (1990); T. Suzuki, A. C. Nairn, S. E. Gandy, P. Greengard, *Neurosci.* 48, 755 (1992)). Although a causal relationship between phosphorylation of APP and its cleavage has not yet been established, purified PKC can directly phosphorylate a synthetic COOH-terminal APP fragment (S. Gandy, A. J. Czernik, P. Greengard, *Proc. Natl. Acad. Sci. U.S.A.* 85, 6218 (1988)). It is also possible that other receptor species linked to phosphatidylinositol turnover, and thus to receptor-coupled generation of diacylglycerol with subsequent activation of PKC, may also regulate APP release. APP release was not stimulated by increased intracellular calcium levels alone, as indicated by the failure of the calcium ionophore A23187 to mimic the receptor-mediated stimulation of basal APP release.

C. Analysis of the APP Fragments Released

Reconstituted culture media proteins corresponding to 150 μg of total cell protein were separated by SDS-polyacrylamide gel electrophoresis on 12% gels and Western blots were performed with the monoclonal antibody 22C11 directed against a purified full-length APP fusion protein (A. Weidemann et al., *Cell*, 57:115 (1989), M. R. Palmert et al., *Proc. Natl. Acad. Sci. USA*, 86:6338 (1989)). Molecular weight standards were obtained from Amersham. Cells were lysed on ice in a buffer containing 2% TRITON X-100, 2% SDS, 0.1 M Tris (pH 6.8), 15% glycerol, EDTA (5 mM), phenylmethylsulfonyl fluoride (2 mM), aprotinin (10 μM), leupeptin (1 μg.ml), pepstatin (0.1 μg/ml), and Tosyl-L-lysine chloromethyl ketone (1 μg, ml), (all from Sigma), ultrasonicated, boiled (5 minutes), and diluted 1:1 in SDS-free loading buffer. Equal amounts of cell protein (20 μg/lane) and media corresponding to 300 μg of total cell protein were separated on 7.5% SDS-polyacrylamide gels, and Western blots performed as described (A. Weidemann et al., *Cell*, 57:115 (1989), M. R. Palmert et al., *Proc. Natl. Acad. Sci. USA*, 86:6338 (1989)). For each treatment group represented on the Western blots, proteins secreted into the conditioned media and cell-associated proteins were obtained from the identical culture dishes.

The immunoreactive bands were compared densitometrically using a LKB Ultroscan laser scanner. Scanning parameters included 40 μm vertical scanning intervals at a total slit width of 2.4 mm (3×0.8 mm), and automatic subtraction of the absorbance offset determined for each blot individually. Measurements were performed in the linear range which was determined using dilution curves of cell protein extracts. Results were normalized to basal APP release from vehicle-treated controls determined within the same blot. Experiments were done with duplicate or triplicate cell culture dishes and repeated 5 to 7 times for statistical analysis with Mann-whitney rank sum tests or analysis of variance and post hoc Scheffe tests as indicated.

The densitometric analysis indicated that receptor activation with carbachol increased the basal APP release 3.9-fold (range: 2.75–6.0; n=7) in the m1 transfected cells, and 5.4-fold (range: 4.1–6.7; n=7) in the m3 transfected cells (FIG. 1a). These results show that cellular APP release can be controlled by cell-surface neurotransmitter activity. Basal release of APP fragments from m2 or m4 mAChR-transfected cells, and from wild-type cell lines was not stimulated by carbachol (FIG. 1A). These results indicate that neurotransmitter-control of APP release is receptor subtype-specific, presumably due to the differential coupling of the receptor subtypes to distinct second messenger systems: activation of the phospholipase C-linked mAChR subtypes m1 and m3 stimulated APP release, whereas the adenyl cyclase-linked subtypes m2 and m4 did not mediate this response (FIG. 1A). E. G. Peralta, A. Ashkenazi, J. W. Winslow, J. Ramachandran, D. J. Capon, *Nature*, 334:434 (1988). The nomenclature for the mAChR subtypes used in this report follows the recommendation of the Muscarinic Receptor Nomenclature Committee, *Trends Pharmacol. Sci.* (suppl.), p. vii (1989). J. Sandmann, E. G. Peralta, R. J. Wurtman, *J. Biol. Chem.*, 266:6031 (1991).

The results of the blots showed that stimulation with carbachol decreased the abundance of cell-associated 141 kD APP, whereas the cell-associated 115 kD APP remained unaffected. The concomitant carbachol-induced increase of a 128 kD APP derivative secreted into the culture medium suggests that the secreted 128 kD protein is a cleavage product of the cell-associated 141 kD APP.

In order to investigate whether the secreted APP fragments were cleavage products of the parent protein lacking the COOH terminus, a polyclonal antiserum against the COOH terminus was used (D. J. Selkoe et al., *Proc. Natl. Acad. Sci. USA*, 85:7341 (1988)). Western blot analysis of cell-associated APP in both m1 and m3 mAChR-transfected cell lines using this antiserum revealed the expected pattern of APP and APP fragments which was similar to that described in human brain cortex (D. J. Selkoe et al., *Proc. Natl. Acad. Sci. USA*, 85:7341 (1988)). This antiserum did not detect any APP fragments in conditioned media obtained from stimulated or unstimulated m1 and m3 transfected cell lines, indicating that the secreted APP fragments are indeed APP cleavage products lacking the COOH terminus.

EXAMPLE 2

Regulation of APP Processing by Bradykinin Receptors

PC-12 cell lines were obtained from American Type Culture Collection (CRL 1721) and grown in Dulbecco's modified Eagle's medium supplemented with 10% horse serum and 2.5% fetal bovine serum at 37° C. under a 5% carbon dioxide atmosphere. Cells were plated on collagen-coated culture dishes. For differentiation into the neuronal phenotype, 50 ng/ml nerve growth factor was added 24 hours after plating and differentiation was verified after three days by neurite outgrowth. Experiments were conducted with subconfluent monolayers approximately five days after plating.

Media were removed from culture dishes; cells were washed twice with serum-free N2 medium and experiments were done at 37° C. on a hot plate in serum-free N2 medium. Media were removed after incubation periods, desalted on sephadex G-25 columns with water as eluent, lyophilized and resuspended in 100 µl sample butter, and boiled for five minutes. Experiments were carried out in triplicate culture dishes and were repeated three to six times.

Cells were treated with 10 µM bradykinin or with vehicle (control) and secretion of APP was assessed over time, using Western blot and densitometry. Equivalents of 4.5 µl resuspended media protein extract per mg cell protein was loaded on each lane of linear SDS-12%-polyacrylamide gels, separated electrophoretically and transferred to polyvinyldifluoride membranes. Membranes were blocked, and probed with monoclonal antibody 22C11. Membranes were washed, and incubated with anti-mouse IgG conjugated to horseradish peroxidase. Bands were visualized with enhanced chemiluminescence using pre-flashed (linear) x-ray films. For densitometric analysis, bands were scanned with a Pharmacia LKB UltroScan XL laser densitometer set at 40 µm vertical interval size and 2.4 m horizontal slit width. Data were normalized to vehicle-treated controls which were always run within the same blots.

Figure 3:
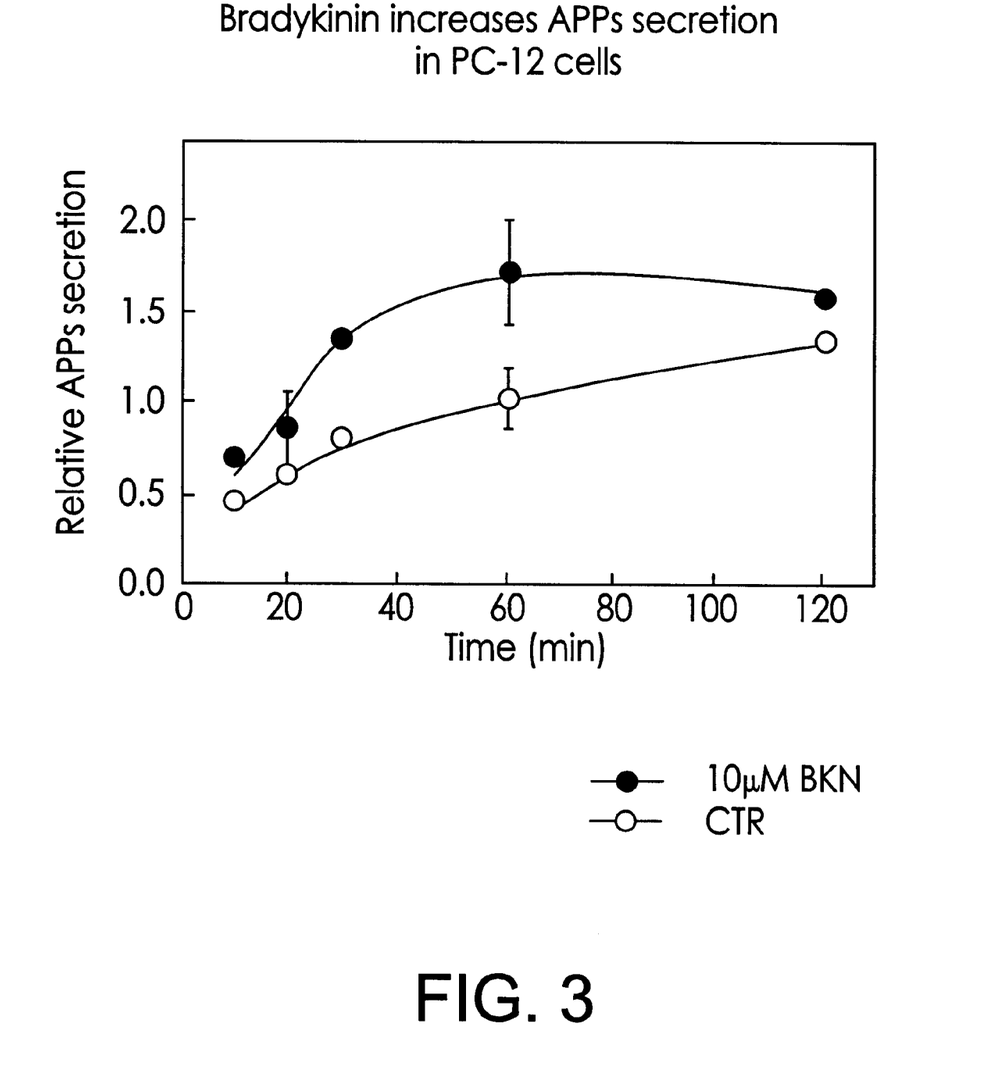
FIG. 3 is a graphic representation of stimulation of secretion of soluble APP (APPs) fragments by PC-12 bradykinin receptors. Filled symbols, bradykinin; open symbols, controls.

As shown in FIG. 3, stimulation of PC-12 bradykinin receptors with bradykinin (BKN) increases the secretion of soluble N-terminal APP derivatives (APPS) into the medium. CTR is the control, in which no bradykinin was added.

Figure 4:
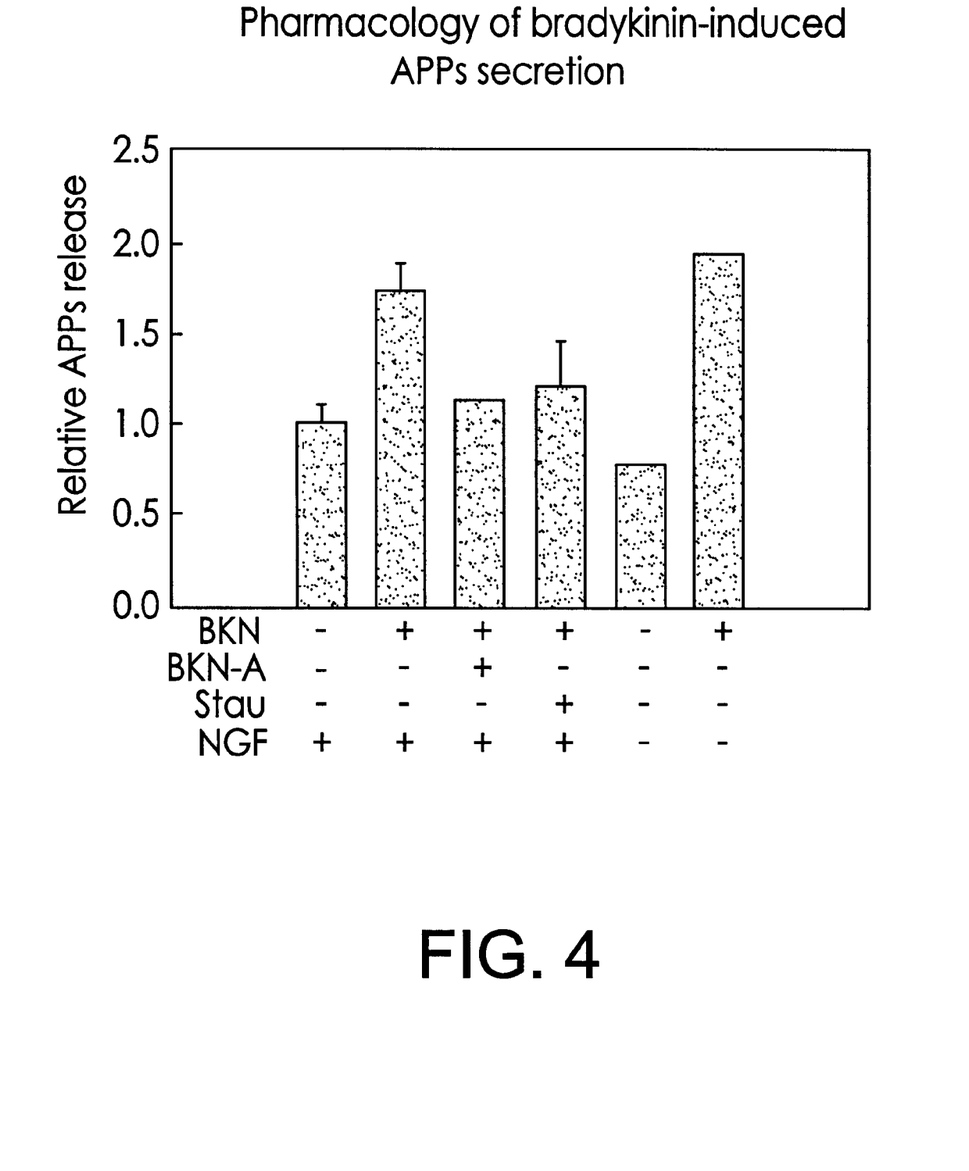
FIG. 4 is a graphic representation of pharmacology of secretion of soluble APP (APPs) fragments by PC-12 cells. BKN=bradykinin; BKN-A=bradykinin receptor antagonist; stau=staurosporine; NGF=nerve growth factor.

Analysis of the pharmacology of bradykinin-induced APPS secretion demonstrates that enhanced secretion is inhibited by addition of a bradykinin receptor antagonist (BKN-A), as well as by addition of the protein kinase blocker staurosporine (Stau). Bradykinin (BKN) also stimulates APP$^s$ secretion in undifferentiated PC-12 cells (those to which nerve growth factor (NGF) was not added). These results are depicted in FIG. 4.

EXAMPLE 3

Regulation of APP Processing by Serotonin Receptor Subtypes

Experimental procedures identical to those described in Example 1 for muscarinic receptors were used to investigate the ability of serotonin receptors to regulate, with the exception that the cells were serum-deprived for 24 hours prior to the stimulation experiments.

Figure 5:
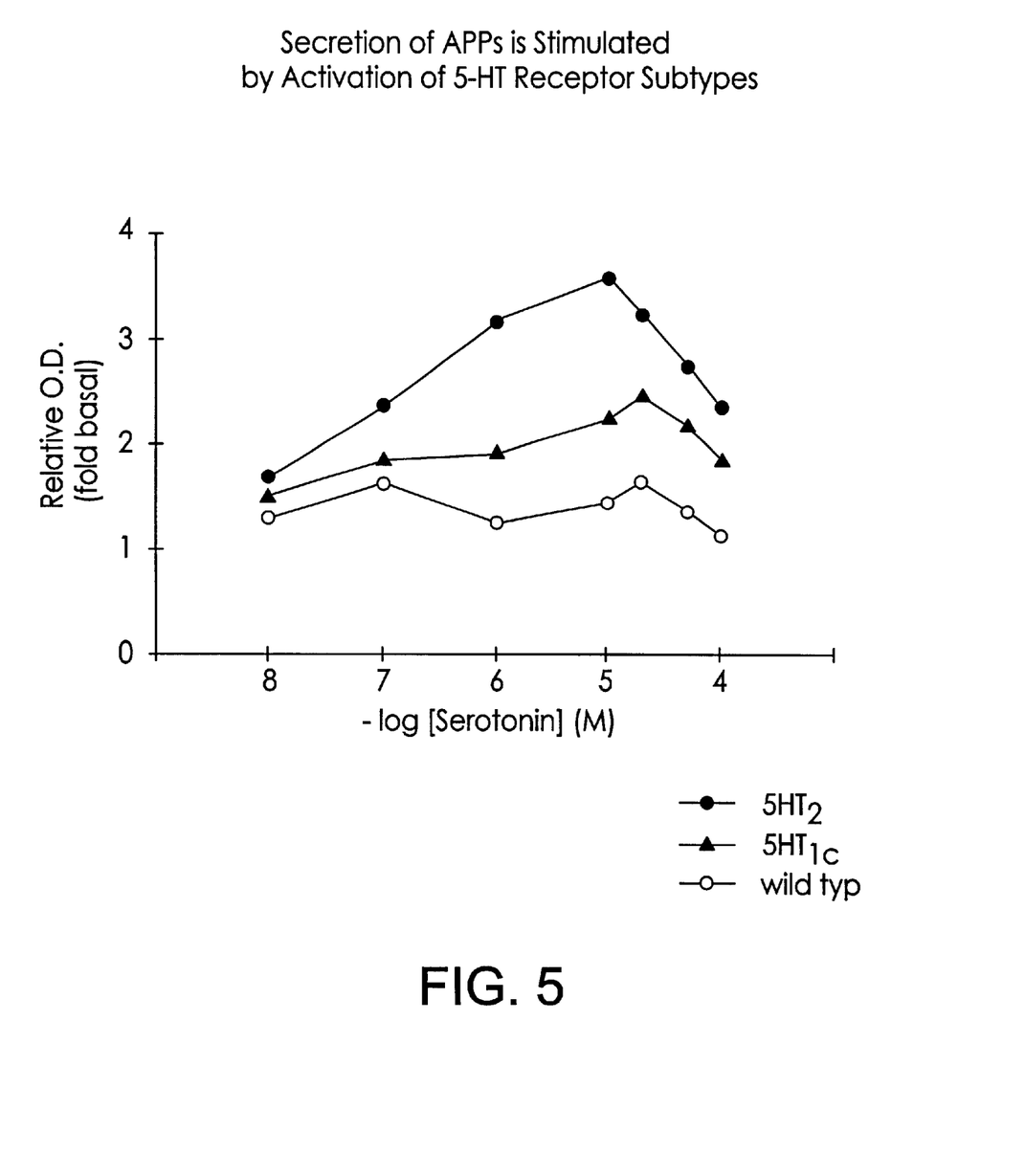
FIG. 5 is a graphic representation of stimulation of soluble APP (APPs) fragments by 5HT receptor subtypes. Filled circles, subtype $5HT_2$; filled triangles, subtype $5HT_{1C}$; open circles, control cells. Data are means of duplicate culture dishes.

3T3 fibroblasts were transfected with cDNA constructs encoding the serotonin receptor subtypes $5HT_2$ or $5HTIC_{1C}$. Control cells were not transfected. The results of the experiment are shown in FIG. 5. Serotonin increased the relative activation of specific serotonin receptor subtypes increases release of N-terminal non-amyloidogenic APP derivatives.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. An assay for identifying an agent which activates a cell surface neurotransmitter receptor which is linked to phospholipase C and protein kinase C, resulting in stimulation of non-amyloidogenic APP processing in the cell comprising the steps of:
   (a) contacting a culture of cells which are transfected with DNA encoding a cell surface neurotransmitter receptor linked to phospholipase C and protein kinase C with an agent to be assessed for its ability to activate cell surface neurotransmitter receptors, thereby generating a test culture;
   (b) incubating the test culture under conditions appropriate for APP processing to occur;
   (c) detecting the level of non-amyloidogenic APP processing derivatives produced by the cells in the test culture, thereby obtaining a test level; and
   (d) comparing the test level with the level of non-amyloidogenic APP processing derivatives produced by the cells of (a) in the absence of the agent,
   wherein if the level of non-amyloidogenic APP processing derivatives produced in the presence of the agent is greater than the level of non-amyloidogenic APP processing derivatives produced in the absence of the agent, the agent is an agent which activates the cell surface neurotransmitter receptor which is linked to phospholipase C and protein kinase C, resulting in stimulation of non-amyloidogenic APP processing.

2. The assay of claim 1 wherein the cells of (a) are human cells and the DNA encodes a neurotransmitter receptor selected from the group consisting of: muscarinic acetylcholine receptors subtype m1 or m3, bradykinin receptors, serotonin receptors subtype $5HT_2$ or $5HT_{1C}$, and other neurotransmitter receptors linked to activation of phospholipase C and protein kinase C.

3. The assay of claim 2 wherein the human cells are embryonic kidney cells.

4. An assay for testing a cholinergic agonist for the capacity to stimulate non-amyloidogenic APP processing, comprising the steps of:
   (a) selecting cells which exhibit normal expression of APP and express endogenous neurotransmitter receptors linked to phospholipase C and a protein kinase C;
   (b) contacting the cells selected in (a) with a cholinergic agonist to be assessed for its ability to activate the endogenous neurotransmitter receptors linked to phospholipase C and a protein kinase C, thereby generating a test culture;
   (c) incubating the test culture under conditions appropriate for APP processing to occur;
   (d) detecting the level of non-amyloidogenic APP processing derivatives produced by the cells in the test culture, thereby obtaining a test level; and
   (e) comparing the test level with the level of non-amyloidogenic APP processing derivatives produced by the selected cells of (a) in the absence of the agent,
   wherein if the level of non-amyloidogenic APP processing derivatives produced in the presence of the cholinergic agonist is greater than the level of non-amyloidogenic APP processing derivatives produced in the absence of the cholinergic agonist, the cholinergic agonist stimulates non-amyloidogenic APP processing.

5. An assay for testing an agent for the capacity to stimulate non-amyloidogenic APP processing comprising the steps of:

(a) transfecting cells which exhibit normal expression of APP with the gene for human muscarinic acetylcholine receptor subtype m1, or the gene for human mucarinic acetylcholine receptor subtype m3, and selecting cells which stably produce m1 receptors or m3 receptors, thereby producing transfected cells which stably produce m1 receptors or m3 receptors;

(b) contacting the transfected cells produced in (a) with an agent to be assessed for its ability to activate the m1 or m3 receptors, thereby generating a test culture;

(c) incubating the test culture under conditions appropriate for APP processing to occur;

(d) detecting the level of non-amyloidogenic APP processing derivatives produced by the cells in the test culture, thereby obtaining a test level; and (e) comparing the test level with the level of non-amyloidogenic APP processing derivatives produced by the transfected cells of (a) in the absence of the agent and with the level of non-amyloidogenic APP processing derivatives produced by non-transfected cells of the same kind which are transfected in (a) and (a) which have been contacted with the agent, wherein if the level of non-amyloidogenic APP processing derivatives produced by the transfected cells in the presence of the agent is greater than the level of non-amyloidogenic APP processing derivatives produced by the transfected cells in the absence of the agent and the level of non-amyloidogenic APP processing derivatives produced by the non-transfected cells in the presence of the agent, the agent is an agent which stimulates non-amyloidogenic APP processing 6. The assay of claim 5 wherein the cells are human embryonic kidney cells.

7. The assay of claim 5 wherein the incubation time for the cultures is between 30 and 60 minutes.

8. The assay of claim 5 wherein the agent to be assessed is a cholinergic agonist.

* * * * *